United States Patent [19]

Colsen et al.

[11] Patent Number: 4,966,164

[45] Date of Patent: Oct. 30, 1990

[54] COMBINED SOUND GENERATING DEVICE AND ELECTRICAL ACUPUNCTURE DEVICE AND METHOD FOR USING THE SAME

[75] Inventors: Ronnie Colsen; Alexander Kairis; Andrew L. Deller, all of Tokyo, Japan

[73] Assignee: Tradatlantex AG, Glaris, Switzerland

[21] Appl. No.: 283,593

[22] Filed: Dec. 13, 1988

[30] Foreign Application Priority Data

Dec. 29, 1987 [JP] Japan ........................ 62-333169

[51] Int. Cl.$^5$ ........................ A61N 1/00

[52] U.S. Cl. ........................ 128/789; 128/907; 131/270; 600/28; 606/32; 606/189

[58] Field of Search ........................ 131/270; 128/419 R, 128/329 R, 329 A, 789, 907; 600/28; 606/32, 167, 185, 189

[56] References Cited

U.S. PATENT DOCUMENTS

| | | | |
|---|---|---|---|
| 2,986,140 | 5/1961 | Gardner et al. | 600/28 |
| 3,140,709 | 7/1964 | Weisz | 600/28 |
| 4,073,296 | 2/1978 | McCall | 128/329 X |
| 4,098,277 | 7/1978 | Mendell | 128/329 A X |
| 4,267,838 | 5/1981 | McCall | 128/907 X |
| 4,311,448 | 1/1982 | Strauss | 131/270 X |
| 4,319,584 | 3/1982 | McCall | 128/907 X |
| 4,450,846 | 5/1984 | McCall | 128/907 X |
| 4,615,681 | 10/1986 | Schwarz | 131/270 X |

FOREIGN PATENT DOCUMENTS

| | | | |
|---|---|---|---|
| 3613736 | 10/1986 | Fed. Rep. of Germany | 128/907 |
| 51-19391 | 2/1976 | Japan . | |
| 110250 | 7/1982 | Japan . | |
| 2165985 | 4/1986 | United Kingdom | 600/28 |

OTHER PUBLICATIONS

McCall, "Aricular ACU Mold Pressure Therapy and ACU Mold Disc Therapy".

*Primary Examiner*—V. Milliaro
*Assistant Examiner*—J. L. Doyle
*Attorney, Agent, or Firm*—Harry W. Barron

[57] ABSTRACT

A device for assisting addiction treatment comprising an earphone adapted to be placed in the external auditory canal of a user's auricle, the earphone having an electrode adapted to contact the surface of the auricle, and a buzzer operable to make sounds of ultra-low frequency, a clip adapted to be attached to the rim of the auricle, the clip having an electrode adapted to contact the rim, a sound generating circuit adapted to deliver low voltage signals of low-frequency to operate the buzzer, and an acupuncture point stimulating circuit adapted to deliver a high voltage stimulus of low current to the electrodes.

27 Claims, 2 Drawing Sheets

COMBINED SOUND GENERATING DEVICE AND ELECTRICAL ACUPUNCTURE DEVICE AND METHOD FOR USING THE SAME

This invention relates to a combined sound-generating device and electrical acupuncture device, and more particularly, to such a device used for assisting addiction treatment and to a method for using the same.

In the past, many proposals for assisting patients to stop smoking have been made, though most have involved either the presence of cigarettes or pseudo-cigarettes. Thus U.S. Pat. No. 2,981,641 discloses the spraying of tobacco with N-alkyl nornicotine to decrease the craving of smokers. U.S. Pat. No. 3,439,685 suggests the addition of a bitter tasting ingredient in tobacco in increasing amounts. U.S. Pat. No. 3,655,325 discloses a pseudo-cigarette packet which, when picked up, emits a coughing sound, to act as a deterrent. U.S. Pat. No. 3,885,576 proposes the use of a wrist band with a mercury switch so connected in a circuit that when a person raises his arm to put a cigarette to his lips, he receives an electric shock. U.S. Pat. No. 3,886,953 and U.S. Pat. No. 3,963,033 disclose a cigarette case with a connection to the smoker's preferred finger, hand or arm, so that manipulation of the case to dispense a cigarette causes an electric shock after a delay, together with an audible alarm. U.S. Pat. No. 4,068,672 discloses a cigarette holder which when placed between a person's lips causes a discharge of low DC current. U.S. Pat. No. 4,246,913 discloses a pressure transducer for a cigarette holder which is used to detect when smoke is drawn from the cigarette and to initiate a small but annoying electric shock to the user. U.S. Pat. No. 4,311,691 suggests the chewing of a gum laden with ethyl maltol in order to render the subsequent smoking of cigarettes less satisfying to the smoker. U.S. Pat. No. 4,620,555 discloses a cigarette dispenser which permits access only after a predetermined time interval which enables the smoker to reconsider the decision to smoke.

The present invention approaches the problem from a rather different direction. In the course of addiction treatment, the patient may suffer withdrawal symptoms and may continue to suffer a nervous desire for the addictive substance, such as nicotine. It is therefore desirable that patients trying to disassociate themselves from addictive substances should have a calm and emotionally stable state of being. A continuous and monotonous rhythmical auditory stimulus helps to obtain such a calm and stable emotional state of being. This phenomenon is neurophysiologically explained by the balancing of the sympathetic and parasympathetic nervous functions, which in turn stabilizes the entire autonomic nervous system. Evidence of this effect is substantiated by the fact that the rhythmical sound of rain drops, or the continuous sound of a running train, offers comfortable stimulation and drowsiness without inducing habituation.

It is a well known fact in Oriental medicine that the auricle and the external auditory canal have electrically sensitive acupuncture points which physiologically correspond to the function of various tissues and internal organs. Western medicine also recognized that the ear is strongly related to the automatic nervous system. For example, it is a widely accepted fact that pouring cooled water into the ear increases the appetite.

Stimulus applied to a certain acupuncture point causes a physiological response from the corresponding internal organ. Electrical current of low frequency has conventionally been used as such stimulus, as it slightly inhibits the activities of the parasympathetic and vagus nerves. Repetitive stimulation over a period of several days causes the brain stem to secrete endogenous opiates, while also causing various glands to secrete endorphins. These opiates and endorphins then serve to relieve pain throughout the body.

Japanese examined patent application Publication No. 57-1100250 discloses an electrically driven device which consists of a musical sound generating unit and a cylindrical vibrating body. A vibrating stimulus is applied to an acupuncture point detected by a probe, and the user simultaneously listens to music to divert his attention from the pain or boredom which might be caused by the mechanical vibrations of the unit.

Japanese examined patent application publication No. 51-19391 discloses an electronic stimulator in the shape of a clip. This device is made from an elastic ring from which a section has been removed and fitted with two electrodes, one of which connects with an acupuncture point when the clip is slipped onto the ear. A current of low frequency is intermittently applied through the electrode to the acupuncture point on the auricle to give treatment to the corresponding tissue or organ in which the patient feels pain.

Both devices apply electronic stimuli to a single acupuncture point on the auricle with the aim of treating a corresponding body tissue or organ. However, few clinical results of success in the application of the above method of treatment have been reported, regardless of the type of stimuli applied to the acupuncture point on the auricle. The combination of music with auricle stimulation is ineffective because music fails to divert the attention of the patient from the electronic pulse, which at times can cause the patient discomfort. Therefore, music is unable to provide the calming effect that is necessary for the success of this method of treatment.

The present invention is intended for the treatment of withdrawal symptoms caused by smoking, alcohol, narcotic drugs, and any other type of addiction. Acupuncture or electrically sensitive points on the skin, including those of the ear, are not directly related to the relief of withdrawal symptoms due to addiction, though endorphins or opiates secreted as a result of acupuncture point stimulation, may relieve withdrawal symptoms. It is certain, however, that acupuncture points with the potential to help cure almost all of the internal organs or tissues of the body exist collectively at the auricle and extended auditory canal. A fetus passes through a growth stage during which it is called a "dwarf", when it has ears proportionately much larger than the rest of the body. This is said to support the reasoning that acupuncture points connected to the KEIRAKU (acupuncture point connecting routes) are centred around the ear, thus enabling the transmission of biochemical instructions to various tissues throughout the body.

It is accordingly an object of this invention to provide a means of suppressing the activities of the parasympathetic and vagus nervous systems by enabling the electronic stimulation of a plurality of acupuncture points of the auricle, thus causing the corresponding internal organs to react against smoking, drinking, and various other forms of addiction, in a biological feedback manner.

It is another object of this invention to enable the provision of effective relief from withdrawal related irritation by means of a monotonous, ultra-low frequency sound in the external auditory canal. This balances the automatic nerve and mitigates the discomfort experienced by patients suffering from addiction related withdrawal symptoms.

It is a further object of this invention to enable the provision of effective relief from withdrawal related anxiety, stress and pain by means of repeated stimulation to the above-mentioned auricle acupuncture points. Such stimulation causes the brain stem to secrete opiates, which in turn reduce the level of discomfort in the addicted patient. The increased level of endorphins in the bloodstream may ease withdrawal symptoms by partially replacing the decrease in the addictive substance with the body's self-produced opiates.

It is a still further object of this invention to provide a highly efficient means of treatment causing no skin or muscle pain in the area, where a low-current, high-voltage electrical pulse is administered.

It is yet another object of this invention to provide a means to help smokers stop smoking. This is achieved by inducing sickness or vomiting when a variety of acupuncture points corresponding to the principal bronchus, oral cavity, stomach and lung are simultaneously stimulated, resulting in the inhibition of peristole, gastric, and salivary secretion. In the case of smoking, a shortage of saliva causes a bad taste as smoke irritates the oral cavity, principal bronchus and lung, thereby triggering coughing. Additionally, swallowed cigarette particles irritate the stomach, throat, and vomiting mechanisms.

It is still another object of this invention to provide a compact device for treatment which is driven by low voltage batteries and housed in a pocket-sized casing. Long battery life is made possible by piezoelectricity and the invention can be applied almost any time, even in the office or on a trip.

More particularly, this invention provides a device by which electrical stimulus may be applied to defined acupuncture points on the auricle which correspond to specific internal organs, immediately after an accoustical stimulus has been applied in the auditory canal.

According to the invention, an auricular device for assisting addiction treatment, comprises an earphone adapted to be placed in the external auditory canal of a user's auricle, the earphone having an electrode, adapted to contact the surface of the auricle, and a buzzer operable to make sounds of ultra-low frequency, a clip adapted to be attached to the rim of the auricle, the clip having an electrode adapted to contact the rim, a sound generating circuit adapted to deliver low voltage signals of low-frequency to operate the buzzer, and an acupuncture point stimulating circuit adapted to deliver a high-voltage stimulus of low current to the electrodes.

Preferably, the earphone electrode is a positive pole electrode and the clip electrode is a negative electrode.

Advantageously, the device includes a selector switch operable sequentially to energise the sound generating circuit and the acupuncture point stimulating circuit.

Conveniently, the earphone has a cup-shaped body and a perforated plate covering the open face of the cup-shaped body.

In this case with advantage, the earphone electrode may be annular and surround the open face of the cup-shaped body.

The earphone electrode may be of electrically conductive rubber.

The clip electrode may be a thin piece of electrically conductive rubber attached to the inside surface of one of two jaw ends of the clip.

The buzzer may comprise a ceramic plate attached to a metal plate mounted in the earphone.

The sound generating circuit may comprise an oscillator having a voltage comparator. Preferably, a contact-confirming circuit supplies the sound generating circuit, and an LED pilot lamp indicates supply to the circuit. For this, the contact-confirming circuit includes a resistor and connections to the ear-phone and clip electrodes to form a voltage divider to compare resistances of the resistor and of the electrical path between the electrodes, the contact-confirming circuit including a voltage comparator to initiate supply to the circuit when the resistance of the path is less than that of the resistor. The oscillator may include a potentiometer consisting of a resistor and a wiper for adjusting the oscillation frequency, preferably within the range 0.5 to 20 Hz.

The acupuncture point stimulating circuit may comprise a high voltage, low current generating circuit, having a transistor on the primary side of an oscillating coil transformer and a rectifier diode and capacitor on the secondary side, and a comparator including a PNPN switch and a diode connected to the output of the generating circuit. The comparator may include a potentiometer consisting of a resistor and wiper for adjusting output voltage, preferably within the range 110 to 120 volts. Conveniently, an LED pilot lamp is connected to indicate the operation of the comparator.

It has been found that the calming effect of the sound waves permits a very mild subsequent electrical stimulation to increase the concentration of natural opioids to a higher level than would occur without such prior sound stimulation. In other words, a higher or more prolonged electrical stimulation would be needed to produce the same amount of natural opioids. Thus the sequential combination of both these types of stimulation produces a greater effect than the use of either or both on their own, and thus provides a synergistic effect to help enable the addict to overcome dependence.

In this respect, the invention extends to a method of assisting addiction treatment, in which sound stimulation is first applied to the auricle, followed by electrical stimulation of the auricular acupuncture points.

A preferred embodiment of this invention consists of a device equipped with an adaptor that fits into the external auditory canal. Attached to this adaptor is an electrically conductive ceramic buzzer, driven by an oscillator circuit, which makes a low-frequency sound of simple rhythm. A positive electrode is directly fitted within said adaptor and a negative electrode, which is supported by a clip, is designed to pressure contact the helix. The acupuncture point stimulating circuit then sends a low-current, high-voltage pulse to the electrodes, between which an electrically energized zone is formed on the auricle. A plurality of acupuncture points scattered around this zone are thus electrically stimulated at the same time to induce a physiological and psychological state to suppress withdrawal symptoms caused by smoking, drinking and various other forms of addiction.

When the electrodes are fastened to the skin, the contact-confirming circuit is operated to confirm secure fastening and then to activate the sound generating circuit and to indicate activation by a green pilot lamp. After the buzzer sound has been heard for some time, the selector switch is moved in order to switch off the sound generating circuit and green pilot lamp. This in turn activates the acupuncture point stimulating circuit, and turns on the red pilot lamp.

How the invention can be carried into effect is hereinafter particularly described with reference to the accompanying drawings, in which:

FIG. 2(*b*) is a perspective view of the buzzer fitted in the earphone of FIG. 2(*a*);

Figure 4:
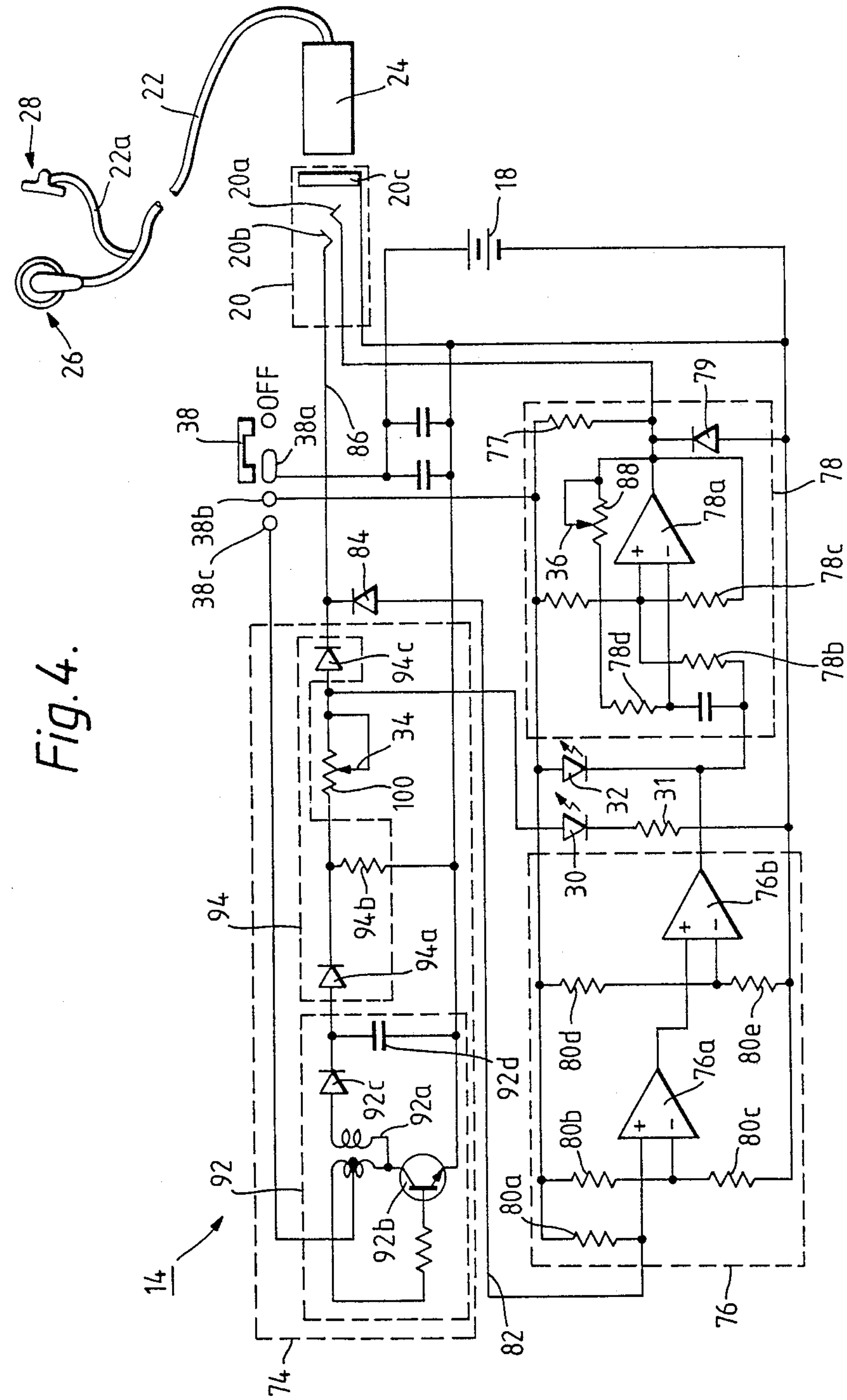
FIG. 4 shows the electrical circuit enclosed in the housing of the embodiment of FIG. 1.

A preferred embodiment (FIG. 1) of an auricular treatment device 10 according to the invention, includes a case 12 made in two parts **12*a* and 12*b* secured together edge-to-edge, as by gluing or screwing. The case 12 is flat and compact enough to be carried in a shirt or jacket pocket for easy personal application. The device 10 includes electrical circuits 14 (FIG. 4) integrated on a circuit board which is enclosed in the case 12. A cutaway portion of the case part 12*a* has a lid 16 to cover a battery compartment where replaceable batteries 18 (FIG. 4) are contained. A jack 20 which accepts a plug 24 on one end of a cable 22, is mounted on the top of the case 12. An ear-phone 26** (FIG. 2*a*) is attached to the other end of the cable 22. A piezo-electric buzzer 46 for auditory stimulation is installed in the ear-phone 26.

The ear-phone 26 has a cup-shaped body 40 with a lead wire outlet 42. Two annular projections inside the body 40 form a ring groove 44, in which is inserted a round diaphragm 48 of a thickness between about 0.2 and 0.4 mm, and preferably 0.3 mm, made from a hard metal, such as nickel. An electrically conductive ceramic plate 50 is attached to the diaphragm 48, and low frequency signals of very low current can be delivered to the ceramic plate 50 from a sound generating circuit through a lead wire 52. The other lead wire 54 is connected to the metal diaphragm 48, and the lead wires 52 and 54 included in the cable 22. The structure and wiring enable the buzzer 46 to emit a rhythmical sound of ultra-low frequency.

The round opening of the cup-shaped body 40 is covered by a thin perforated screen 56 made of aluminium, and an annular electrode 58 made of electrically conductive rubber is mounted around it. After the user has heard a low-frequency sound of simple rhythm, pulse signals of a high voltage and very low current, generated in an acupuncture point stimulating circuit, are applied to the annular electrode 58 through a lead wire 60 included in the cable 22 and attached to the electrode 58.

Figure 3:
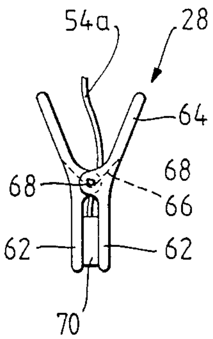
FIG. 3 is a side view of the clip portion of the embodiment of FIG. 1.

The lead wire 54 is branched from the cable 22 between the ear-phone 26 and the jack 20 to form a wire **54*a* of another cable 22*a*. This cable 22*a* connects to a clip 28 containing a negative electrode 70 of electrically conductive rubber, which can be attached to the rim of the user's auricle at any desired location. The clip 28 (FIG. 3) includes a pair of jaw ends 62 with handles 64 pivoted at their centres by a pivot pin 68 and urged by a coil spring 66 in a direction to hold the jaw ends 62 together. The electrode 70 is attached to the inside of one jaw end 62 and the negative lead 54*a* in the cable 22*a* is connected to the electrode 70. The electrically conductive rubber electrode 70 can then be attached to a pressure contact surface area via a metal membrane. The clip 28 is intended to be fastened to the rim of the user's auricle (FIG. 1) so that the electrode 70 contacts the surface of the ear. The ear-phone 26 is intended to be inserted into the ear hole or external auditory canal, so that the electrode 58 makes contact with the skin there. In these positions, the electrodes 58 and 70 are electrically connected by an electrical path 96** which includes acupuncture points and low resistance KEIRAKU or tissue routes in the muscles.

In the top central part of the case 12 are pilot lamps in the form of a red LED 30 and a green LED 32. Sliders 34 and 36 for the wipers of potentiometers, are mounted in the tops of the front and rear parts **12*a* and 12*b* of the case 12, respectively. A slider 38 for a three-position selector switch is fitted on the other side of the top of the case 12 to the jack 20**.

One or other of the electrical circuits 14 (FIG. 4) can be connected to the two 1.5 V batteries 18 by the slider 38 of the selector switch to activate a contact-confirming circuit 76 and a sound generating circuit 78 for the buzzer 46, or an auricle acupuncture point stimulating circuit 74 for the electrode 70. With the selector switch slider 38 in a first operative switch position, a positive output **38*a* from the batteries 18 is connected to a power input 38*b* of the contact-confirming circuit 76 and the sound generating circuit 78. With the selector switch slider 38 in a second operative switch position, the output 38*a* is connected to a power input 38*c* for the stimulus generating circuit 74. When the slider 38** is in a third OFF position, no connections are made.

The contact-confirming circuit 76 is made up of two voltage comparators **76*a* and 76*b* made of I.C. elements, and resistors 80*a*, 80*b*, 80*c*, 80*d* and 80*e*. When the slider 38 of the selector switch is in the first operative switch position, electrical power is applied to the comparator 76*a* through resistors 80*a*, 80*b* and 80*c*. The resistance of the resistor 80*a* is much greater than that of the resistor 80*b*, and the resistance of the resistors 80*b* and 80*c* are equal. In one example, the resistance of resistor 80*a* is 15 Megohms and that of resistor 80*b* is 10 kilo-ohms. Thus the negative input of the comparator 76*a* is connected through the resistor 80*b* to the positive side of the battery 18 and to the negative side of the battery 18 through the resistor 80*c*. The positive input of the comparator 76*a* is connected through the resistor 80*a* to the positive side of the battery 18 and through a line 82 and diode 84 to an output line 86 of the acupuncture point stimulating circuit 74 leading to a contact 20*b* of the jack 20, and thus to the electrode 58. The electrode 58 is connected to the electrode 70 through the electrical path 96 and the electrode 70 is connected by wires 54*a* and 54 to a contact 20*c* of the jack 20. The contact 20*c* is connected to the negative side of the battery 18. The resistor 80*a* and the electrical path 96 form a voltage divider to the positive input of the comparator 76*a*. The output of the comparator 76*a* is connected to the positive input of the comparator 76*b*. The negative input of the comparator 76*b* is connected directly through a resistor 80*d* to the contact 38*b* and through a resistor 80*e* to the negative side of the battery 18. The resistances of the resistors 80*b*, 80*c*, 80*d* and 80*e*** are equal.

The green LED lamp 32 is connected on one side to the power input 38b of the circuit 72 and on the other side to the output of the comparator 76b.

With the ear-phone 26 correctly inserted and the clip 28 properly connected, the resistance of the electrical path 96 should be less than that of the resistor 80a. If this is the case, the positive input to the comparator 76a will be at a lower voltage than the negative input, the resistors 80b and 80c being of equal resistance. Then the comparator 76a will produce an output to the positive input of the comparator 76b so that an output is obtained from this to the green LED lamp 30 and to the sound generation circuit 78. If no such output is obtained, the ear-phone 26 and/or clip 28 is adjusted until an output is obtained indicating that proper contact with the ear has been obtained.

The sound generation circuit 78 includes a voltage comparator 78a whose positive input is from the output of the comparator 76b through a resistor 78b and through a feedback resistor 78c from the output of the comparator 78a. The resistors 78b and 78c are of equal resistance, for example 100 kilo-ohms. The negative input of the comparator 78a is through a capacitor 78d from the output of the comparator 76b, and from the output of the comparator 78a through a potentiometer including a resistor 88 and slider 36 and a resistor 78d. The output of the comparator 78a is connected to the power input 38b through a resistor 77, to the negative pole of the batteries 18 through a diode 79, and to the contact 20a of the jack 20. The oscillator output is fed through the plug 24 and the lead wire 52 in the cable 22 to the ceramic plate 50 which is installed on the diaphragm 48 in the buzzer 46. The return route of the buzzer signal is from the metal diaphragm 48 through the lead wire 54 and plug 24 to the contact 20c in the jack 20 connected to the negative pole of the sound generating circuit 72 and of the batteries 18.

With the clip 28 and electrode 70 on the rim of the ear, and the earphone 26 and electrode 58 in the earhole, a circuit is completed by moving the selector switch slider 38 to the first operative switch position, from the positive pole of the batteries 18, through the contacts 38a and 38b of the selector switch, the resistors 80a, 80b, 80c, 80d and 80e to energise the comparators 76a and 76b. The output of the contact-confirming circuit 76 lights up the green LED lamp 32 and energises the sound generation circuit 78 when proper contact with the ear is confirmed by the resistance of the path 96 being less than that of resistor 80a. The circuit 78 delivers low frequency, very low current signals of 5 to 20 Hz through the contacts 20a and 20c of the jack 20 to buzzer 46. Rhythmical sounds of low frequency are then made by the buzzer 46 and heard by the patient into whose earhole the earphone 26 is inserted. The oscillating frequency is adjustable within the range from 5 to 20 Hz by moving the slider 36 of the potentiometer including the resistor 88.

The acupuncture point stimulating circuit 74 is energized if the slider 38 of the selector switch is moved to the second operative switch position, in which the contacts 38a and 38c are connected. The circuit 74 includes a high-voltage pulse generating circuit 92, a comparator 94 and a potentiometer. Energy from the batteries 18 is fed into the primary side of an oscillating transformer 92a. The combination of a transistor 92b, rectifier diode 92c and capacitor 92d induces a sharp pulse output signal of 110 to 120 volts in the secondary side of the oscillating transformer 92a. The pulse output is rectified by the diode 92c and then applied to the comparator 94, which consists of a PNPN switch 94a, a resistor 94b and a diode 94c. Between the resistor 94b and the diode 94c a potentiometer is connected comprising a resistor 100 and the slider 34. There is also a connection to one side of the red LED lamp 30 whose other side is connected through a resistor 31 to the negative pole of the batteries 18. The pulse can be adjusted by operation of the slider 34. The comparator levels the input signal to a desired voltage and delivers an electrical pulse at peak waveform. This weak but high-voltage pulse signal is sent to the electrode 58 through the contact 20b of the jack 20. With the clip 28 and electrode 70 on the rim of the ear and with the earphone 26 inserted in the earhole or external auditory canal, the electrical path 96 (FIG. 1) is formed between the electrode 58 and the electrode 70 which is in pressure contact with part of the ear. In the electrical path 96 in the ear, lie an acupuncture point 98a for the oral cavity, an acupuncture point 98b for the lung and an acupuncture point 98c for the stomach, as well as many others. These acupuncture points receive strong stimulus from a high-voltage electrical current which causes no pain to the user. The return path from the electrode 70 passes through the cable 22a, cable 22 and the contact 20c of the jack 20, which is connected to the negative pole of the batteries 18. The slider 34 is used to move the wiper of potentiometer on the resistor 100 included in the acupuncture point stimulating circuit 74 for adjustment of the output pulse system.

In operation the slider 38 of the selector switch is moved to the first operative width position. The earphone 26 is inserted into the earhole or external auditory canal and the electrode 70 is placed in contact with the ear by fastening the clip 28 to a part of the rim. When the contact-confirming circuit 76 indicates that these are correctly positioned, the green LED detector lamp 32 comes on. Immediately after the green LED detector lamp 32 is lit, the comparator 78a forms rectangular shaped voltage waves, amplifies the voltage to some degree and the buzzer 46 is driven piezo-electrically to make a simple rhythmic sound of 5 Hz. The frequency may be increased up to 20 Hz by moving the potentiometer wiper slider 36, by which the user is able to set the frequency to the level which is most comfortable for him. The buzzer 46 is turned off manually after 2 to 4 minutes by moving the slider 38 of the selector switch to the second operative switch position. The acupuncture point stimulating circuit 74 is then activated for treatment. At this time the red LED lamp 30 comes on. The recommended treatment time is 2 to 3 minutes. When the acupuncture point stimulation circuit 74 is operational, the acupuncture points 98c, 98b and 98a for the stomach, lung and oral cavity, respectively, as well as others in the electrical path 96 (FIG. 1) are simultaneously stimulated by a high-voltage, low-current electrical pulse. Treatment is discontinued by moving the slider 38 of the selector switch to the third or OFF position. Continued auditory stimulus can be obtained by moving the slider 38 to the first operative switch position.

The treatment starts with hearing an ultra-low frequency sound of simple rhythm, which is followed by the application of a high-voltage electrical stimulus to the acupuncture points of the ear. As daily treatment continues, smokers who practice the treatment may start vomiting, feeling sick and beginning to cough, as they smoke. They then come to dislike the taste of smoking and, finally, they avoid smoking altogether. If the treatment continues, opiates produced in the body will relieve withdrawal symptoms and the user will be able to cease smoking, provided that he or she has the desire to do so.

In principle, the invention functions to provide a means of relaxation enabling the user to overcome this agitation associated with withdrawal from the addiction particularly to smoking. It can be self-administered anywhere and at any time. It functions to provide soothing auditory and electrical stimuli according to parameters of the electrical resistance of the skin. Different states of relaxation give rise to different electrical skin resistance values. The user can regulate the intensity and frequency of the stimuli according to the response in the form of relaxation. Initially, three daily treatments of six minutes each are suggested, with three minute treatments when a strong urge to smoke is felt, Therapy is usually complete in four to six weeks, but may be continued until sufficient relief from the physiological and emotional symptoms of addiction is obtained.

Figure 1:
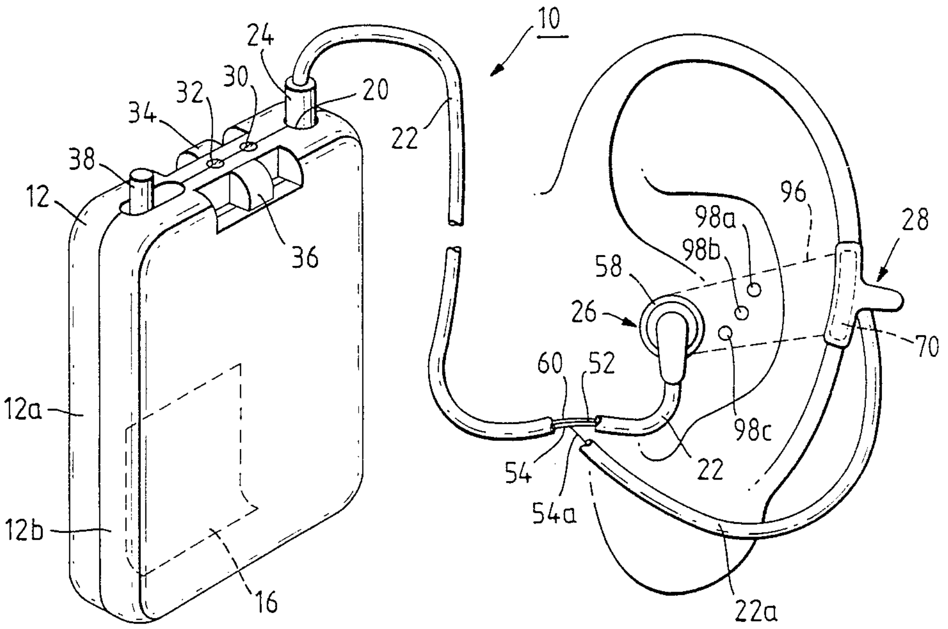
FIG. 1 shows a preferred embodiment of this invention with connections to the ear of the user.
Figure 2A:
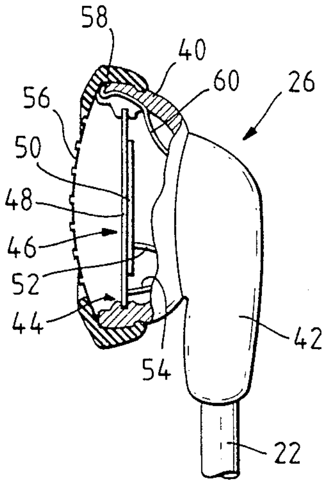
FIG. 2(*a*) is a side view, partly in section, of the earphone portion of the embodiment of FIG. 1.
Figure 2B:
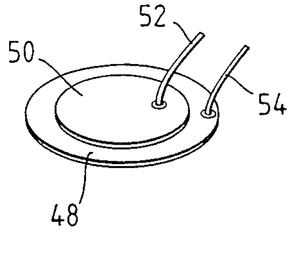

As shown in FIG. 1, the clip is fastened to the rim of the ear slightly higher than the level of the earphone, which is placed in the earhole or auditory canal. This position is recommended for those who are addicted to nicotine. The clip should be fastened a little higher than the stop-smoking position to cope with other narcotic addictions. The clip position recommended for those addicted to alcohol is located at the same level as the earphone in the earhole.

The preferred embodiment of this invention consists of a device with an earphone which is mounted in the earhole or external auditory canal, the electrode of the adaptor is directly connected to the acupuncture points for the stomach, the lung, or the oral cavity for the same curative results.

The contact-confirming circuit 76 may be located in the ear-phone 26.

Use of this invention for the purpose of helping the user refrain from alcohol, smoking and narcotic addiction is primarily described in the specification. However, this device can also be used to treat other illnesses by shifting the clip position, as the acupuncture points corresponding to almost all bodily tissues and internal organs are concentrated in the auricle and the external auditory canal.

A device according to this invention can be equipped with a timer so that the length of the buzzer sound and acupuncture point stimulus is automatically timed.

We claim:

1. A combined sound-generating device and electrical acupuncture device, said sound-generating device comprising an earphone and a sound generating circuit, said earphone having a buzzer operable to make sounds of low-frequency and said sound-generating circuit being adapted to deliver low voltage signals of low-frequency to operate said buzzer, said earphone additionally having a first electrode adapted to contact the surface of said auricle and forming part of said electrical acupuncture device, said electrical acupuncture device also including a clip adapted to be attached to the rim of said auricle, said clip having a second electrode adapted to contact said rim, and an acupuncture point stimulating circuit adapted to deliver a high voltage stimulus of low current to said electrodes, said first and second electrodes being oppositely charged.

2. A device as claimed in claim 1, in which the earphone electrode is a positive pole electrode and the clip electrode is a negative pole electrode.

3. A device as claimed in claim 1, including a selector switch operable sequentially to energise the sound generating circuit and the acupuncture point stimulating circuit.

4. A device as claimed in claim 1, in which the earphone has a cup-shaped body and a perforated plate covering the open face of the cup-shaped body.

5. A device as claimed in claim 1, in which the earphone electrode is annular and surrounds the open face of the cup-shaped body.

6. A device as claimed in claim 1, in which the earphone electrode is of electrically conductive rubber.

7. A device as claimed in claim 1, wherein the buzzer comprises a ceramic plate attached to a metal plate mounted in the earphone.

8. The device as claimed in claim 1 wherein said clip comprises two jaw ends and the clip electrode is a thin piece of electrically conductive rubber attached to the inside surface of one of said two jaw ends.

9. A device as claimed in claim 1, wherein the sound generating circuit comprises an oscillator having a voltage comparator.

10. A device as claimed in claim 9 including a contact-confirming circuit to supply the sound generating circuit.

11. A device as claimed in claim 10, in which the contact-confirming circuit includes a resistor and connections to the electrodes to form a voltage divider to compare resistances of the resistor and of the electrical path between the electrodes, the circuit including a voltage comparator to initiate supply to the circuit when the resistance of the path is less than that of the resistor.

12. A device as claimed in claim 11, including an LED pilot lamp to indicate supply to the circuit.

13. A device as claimed in claim 9, wherein the oscillator includes a potentiometer consisting of a resistor and a wiper for adjusting the oscillation frequency.

14. A device as claimed in claim 1, wherein the acupuncture point stimulating circuit comprises a high voltage, low current generating circuit having a transistor on the primary side of an oscillating coil transformer and a rectifier diode and a capacitor on the secondary side, and a comparator consisting of a PNPN switch and a diode connected to the output of the generating circuit.

15. A device as claimed in claim 14, wherein the comparator includes a potentiometer consisting of a resistor and a wiper for adjusting output voltage.

16. A device as claimed in claim 14, including an LED pilot lamp to indicate operation of the comparator.

17. A method of assisting treatment, in which sound stimulation is first applied to the auricle, followed by electrical stimulation of the auricular acupuncture points, in the absence of sound stimulation.

18. A device for treatment of a user comprising:

first electrode means positioned in the canal of one ear of said user and making electrical contact with said canal surface;

second electrode means affixed in electrical contact with said user in a position such than any current which flows between said first electrode means and said second electrode means flows through the auricular acupuncture points of said user;

sound wave generating means within said first electrode means for providing sound energy into said canal in response to control signals provided thereto; and electrical means coupled to said first and second electrode means for selectively providing current to flow between said first and second electrode means and for selectively providing said control signals to said sound wave generating means.

19. A device as claimed in claim 18 in which said first electrode means is located on an earphone and said second electrode means is located on a clip adapted to be attached to the rim of the oracle.

20. A device as claimed in claim 18 wherein said electrical means includes a selector switch operable sequentially to energize said sound wave generating means and the current flow providing means between said first and second electrode means.

21. A device as claimed in claim 19, in which the earphone has a cup-shaped body and a perforated plate covering the open face of the cup-shaped body.

22. A device as claimed in claim 21, in which said first electrode means is annular and surrounds the open face of the cup-shaped body.

23. A device as claimed in claim 19, wherein said clip comprises two jaw ends and said second electrode means is a thin piece of electrically conductive rubber attached to the inside surface of one of said two jaw ends of said clip.

24. A device as claimed in claim 18, wherein the said sound wave generating means includes an oscillator having a voltage comparator.

25. A device as claimed in claim 24 including a contact-confirming circuit to supply said sound wave generating means.

26. A device as claimed in claim 25 in which the contact-confirming circuit includes a resistor and connections to said first and second electrode means to form a voltage divider to compare resistances of the resistor and of the electrical path between said first and second electrode means, said contact-confirming circuit including a voltage comparator to initiate supply of said sound wave generating means when the resistance of said path is less than that of said resistor.

27. A device as claimed in claim 26, including an LED pilot lamp to indicate supply to the said sound wave generating means.

* * * * *